United States Patent [19]

van der Burg

[11] 4,062,848
[45] Dec. 13, 1977

[54] TETRACYCLIC COMPOUNDS

[75] Inventor: Willem Jacob van der Burg, Heesch, Netherlands

[73] Assignee: Akzona Incorporated, Asheville, N.C.

[21] Appl. No.: 669,544

[22] Filed: Mar. 23, 1976

[30] Foreign Application Priority Data

Apr. 5, 1975 Netherlands .................. 7504075

[51] Int. Cl.$^2$ ............................................. C07D 471/22
[52] U.S. Cl. ........................ 260/268 PC; 260/256.4 F; 260/256.5 R; 260/294.8 A; 260/296 P; 424/250; 424/251; 424/263
[58] Field of Search ............. 260/268 PC, 256.4 F, 260/296 P, 256.5 R, 294.8 A

[56] References Cited

U.S. PATENT DOCUMENTS 3,534,041  10/1970  van der Burg et al. ........ 260/268 PC
3,959,470  5/1976   Mashkovsky et al. ......... 260/268 PC

OTHER PUBLICATIONS

Burger (ed.), Medicinal Chemistry, Third Ed., Wiley--Interscience, N.Y., pp. 1643-1662, 1970.

*Primary Examiner*—R. J. Gallagher

*Attorney, Agent, or Firm*—Robert H. Falk; Francis W. Young; Charles A. Wendel

[57] ABSTRACT

The invention relates to compounds of the general formula I:

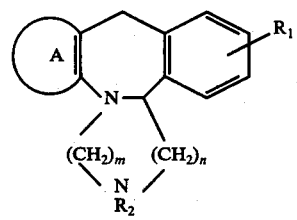

or a salt thereof, in which

A represents a pyridine ring or a halogen substituted pyridine ring, $R_1$ represents hydrogen, alkyl (1-6 C), alkoxy (1-6 C), alkylthio (1-6 C), halogen, OH, SH or $CF_3$ $R_2$ represents hydrogen or a lower alkyl or aralkyl group and n and m may each be 1, 2 or 3 with the proviso that the sum of m and n must be 2, 3 or 4, having CNS activity, a pronounced antihistamine activity and little or no antiserotonin activity.

4 Claims, No Drawings

TETRACYCLIC COMPOUNDS

The invention herein referred to relates to novel biologically active tetracyclic compounds, to methods for the preparation of these compounds and to methods for the preparation of pharmaceutical formulations containing these compounds as active components.

The invention relates to particular to the compounds of the general formula I:

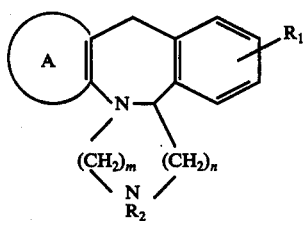

I or a salt thereof, in which

A represents a pyridine ring or a halogen substituted pyridine ring, $R_1$ represents hydrogen, alkyl (1-6 C), alkoxy (1-6 C), alkylthio (1-6C), halogen, OH, SH or $CF_3$ $R_2$ represents hydrogen or a lower alkyl or aralkyl group and n and m may each be 1, 2 or 3 with the proviso that the sum of $m + n$ must be 2, 3 or 4.

The compounds of general formula I possess valuable biological properties: they possess in particular CNS activity and pronounced antihistamine activity, but have little or no antiserotonin activity.

The compounds according to the invention may be prepared in a way which is usual for such compounds.

The present compound I may for example be prepared by ring closure of a compound with the general formula:

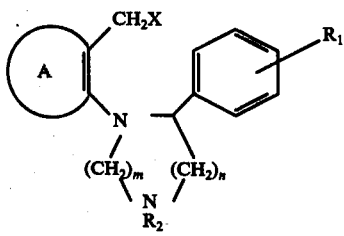

II or a salt thereof, in which A, $R_1$, $R_2$, n and m have the previously indicated meanings and X represents a hydroxyl group, an esterified or etherified hydroxyl group or hydrogen (F, Cl, Br or I). The etherified hydroxyl group may preferably be a lower alkyloxy group (1-6 C); the esterified hydroxyl group is preferably a lower aliphatic acyloxy group, such as an acetoxy group, or a sulphonyloxy group, such as a tosyloxy or mesyloxy group.

This condensation is performed under strongly dehydrating (X = OH) or dehydrohalogenating (X = halogen) conditions, preferably at an elevated temperature.

Dehydrating, or as the case may be, dehydrohalogenating agents, which may be added to the reaction mixture for this purpose include acids, such as sulphuric acid, concentrated hydrochloric acid, picric acid, trifluoroacetic acid, phosphoric acid, polyphosphoric acid (PPA), phosphorus oxychloride, phosphorus trioxide, phosphorus pentoxide and Lewis acids, such as aluminium chloride, ferric chloride, zinc chloride, tin chloride, titanium chloride, boron trifluoride, antimony pentachloride and zirconium tetrachloride.

Dehydrating agents which are particularly preferred are sulphuric acid and phosphorus derivatives, such as PPA and phosphorus oxychloride. As dehydrohalogenating agent, use is preferably made of aluminium chloride. This method is preferably used for the preparation of compounds in which m and n do not both simultaneously have the value 1.

The compounds of general formula II are new compounds, which may be prepared in a variety of ways.

The flow sheet on page 6 (sheet A) shows one of the possible routes for the preparation of the starting-material II. The steps given all refer to reactions which are in themselves known in the literature.

Another method of preparation, which in view of the substantially analogous method of preparation of the starting material is in fact to some extent related to the method noted above, consists of the reduction of the keto group in a compound of general formula III:

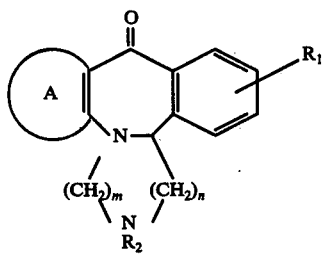

III in which A, $R_1$, $R_2$, m and n are defined before.

The reduction of the keto group to the corresponding methylene group is achieved in a way usual for such conversions, for example, by a Wolff-Kishner, Huang-Minlon or Clemmensen reduction. However, also other methods can be used, such as reducing the keto group to a hydroxyl group with e.g. a complex metalhydride, followed by removal of the hydroxyl group in a known manner e.g. by converting the hydroxyl group into a suitable ether such as a tetrazolyl ether, or into a suitable ester such as an ester derived from a sulphonic or phosphoric acid, or into halogen and splitting off these groups by hydrogenolysis, converting the keto group to a di-alkylthioketal or alkylenethioketal, followed by hydrogenolysis.

The compounds III are also new compounds, and are prepared in a way usual for such compounds. By making a simple change in the reaction scheme as shown for the starting materials II, the compounds III may also be prepared (see Flow Sheet A).

Flow Sheet A; compound II and III

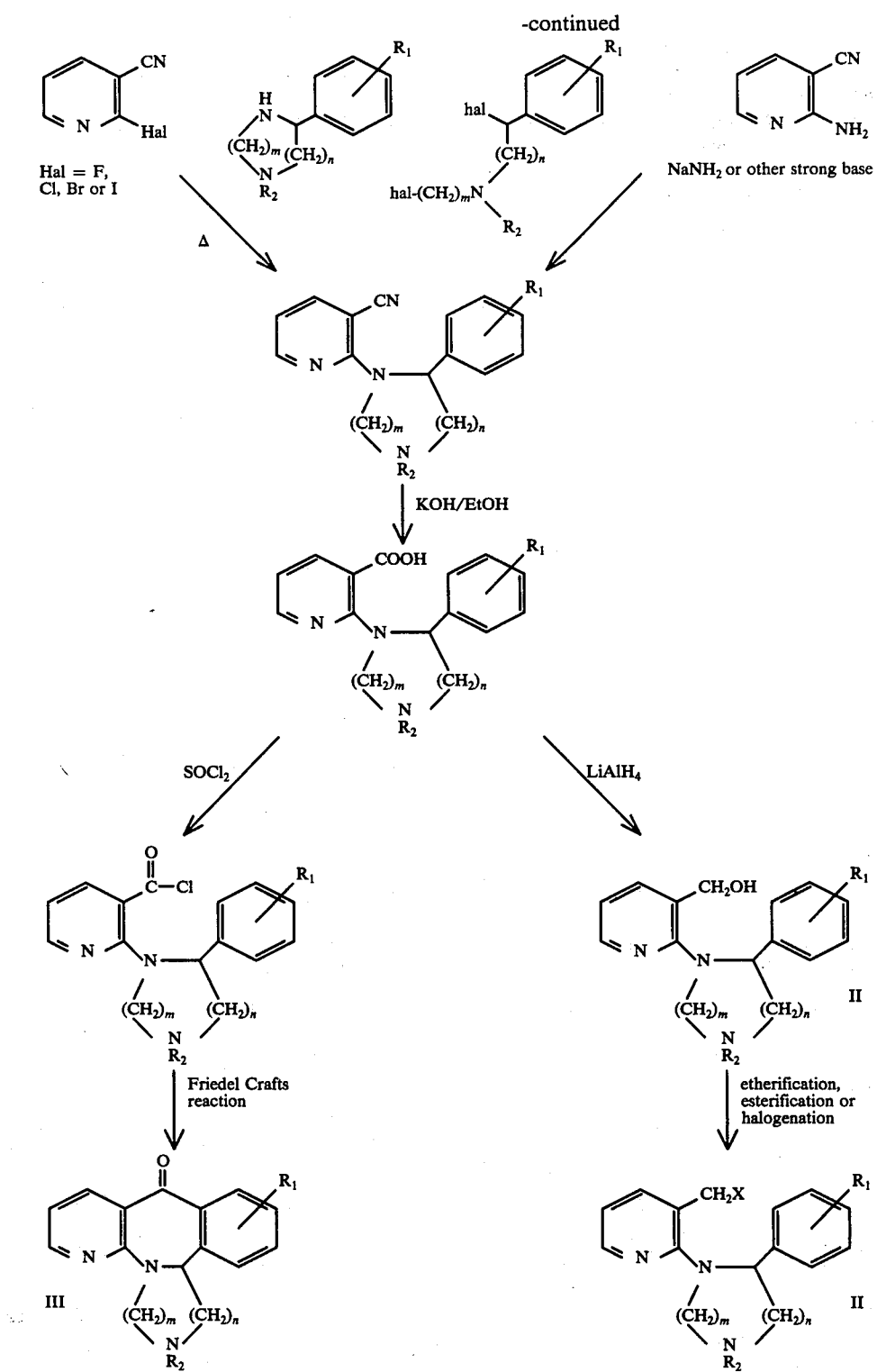
A completely different but readily usable method for the preparation of the present compounds consists of the ring closure of a compound with the general formula IV:

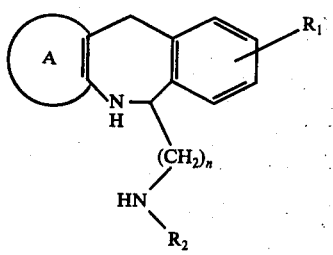

or a salt thereof, where A, $R_1$, $R_2$ and $n$ possess the meanings previously defined.

The ring closure for obtaining the heterocyclic ring (ring D) may take place in the way described in the literature, by allowing the compound IV to react with a reagent of general formula V:

$$Z_1-(CH_2)_m-Z_x \qquad V$$

where $m$ has the meaning previously defined, and $Z_1$ and $Z_2$ represent similar or different groups selected from halogen, hydroxy or an etherified of esterified hydroxy group, such as a lower alkyloxy group, a lower aliphatic acyloxy group or a sulphonyloxy group.

Examples of reagent V which may be used in the method herein referred to are methylene chloride, methylene bromide, ethylene bromide, ethylene iodide, ethylene chloride, 1-chloro-2-bromo-ethane, propylene chloride, propylene bromide, methylene diol (= solution of formaldehyde in water), 1-tosyloxy-3-bromopropane, 1,3-dimesyloxy-propane etc.

A related method for preparing the relative compounds consists of a ring closure of a compound of the formula:

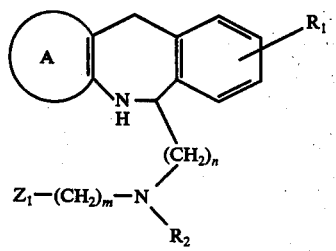

or a salt thereof, in which $Z_1$, $R_1$, $R_2$, A, $m$ and $n$ have the meanings defined previously.

In general, this ring closure is effected at an elevated temperature, preferably in the presence of a ring closure-promoting agent. In the case $Z_1$ is hydroxy, the ring closure may be promoted by adding a dehydrating agent herein defined previously. If $Z_1$ is halogen the ring closure is preferably carried out by adding a base such as pyridine or triethylamine.

The starting compounds of formula VI may be isolated from the reaction described in the previous method using a compound of formula IV and a reagent V as starting products. Usually, however, they may be prepared more conveniently in a way indicated in Flow Sheet B.

Another method for the preparation of the compounds according to the invention consists of reduction of one or more oxo- or thio group(s) in a compound of general formula:

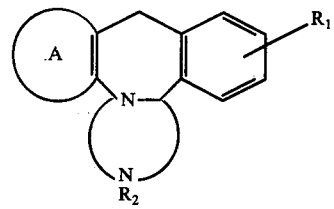

on a salt thereof, in which A, $R_1$, $R_2$ have the meanings defined above, and B represents - in agreement with the definition of $m$ and $n$ of formula I - a five-, six- or seven-membered heterocyclic ring, in which at least one of the carbon atoms adjacent to one of the nitrogens is substituted by an oxo or thio group.

The reduction of the above described compound is achieved in a way usual for the reduction of an amide or thio-amide group, with the aid of a metal hydride, such as lithium aluminium hydride, diborane, or by means of catalytic hydrogenation, preferably with Raney nickel. Diborane is the preferred reducing agent.

Compounds VII may be prepared in a way analogous to that described in the literature, by condensation of a diamine of the general formula IV or a related compound according to the formula IV A, mentioned in the flow sheet on page 12, with reagents such as carbon disulphide ($m = 1$), phosgene, ($m = 1$), thiophosgene ($m = 1$), urea ($m = 1$), an alkyl haloformate ($m = 1$), a dialkyl oxalate ($m = 2$), a halo-thio-acetyl halide ($m = 2$), an alkyl halo-acetate ($m = 2$), acrylic acid/-$POCl_3$ ($m = 3$), a halopropionyl halide ($m = 3$), etc.

Starting from a compound of formula IV A it is also possible to obtain compounds of formula VII by reacting IV A with a reagens of formula V, especially formaldehyde (= methylene-diol).

The starting materials of the general formulae IV, IV A and VI needed in the last mentioned reaction methods are prepared in a manner known for analogous compounds. A method for obtaining these compounds is outlined in Flow Sheet B.

The compounds I possess an asymmetric carbon atom, as a result of which separate optical antipodes may also be prepared in addition to a racemic mixture I. These optical antipodes, which, just as the racemic mixture I, are included in the invention, may be prepared by resolution of a racemic final product I. They may however also be prepared directly by starting from optically active precursors with formula II, III, IV, VI or VII instead of the corresponding racemic starting material. This last-noted synthesis means in fact that the resolution of the racemates has taken place in an earlier stage of the total synthesis.

By salts of the compounds according to the invention are understood: the pharmaceutically acceptable acid addition salts and quaternary ammonium compounds I.

The acid addition salts are obtained by reaction of the free base I with a suitable inorganic or organic acid, such as hydrochloric acid, sulphuric acid, phosphoric acid, acetic acid, maleic acid, fumaric acid, citric acid, ascorbic acid etc.

Flow sheet B; compounds IV, IV A and VI
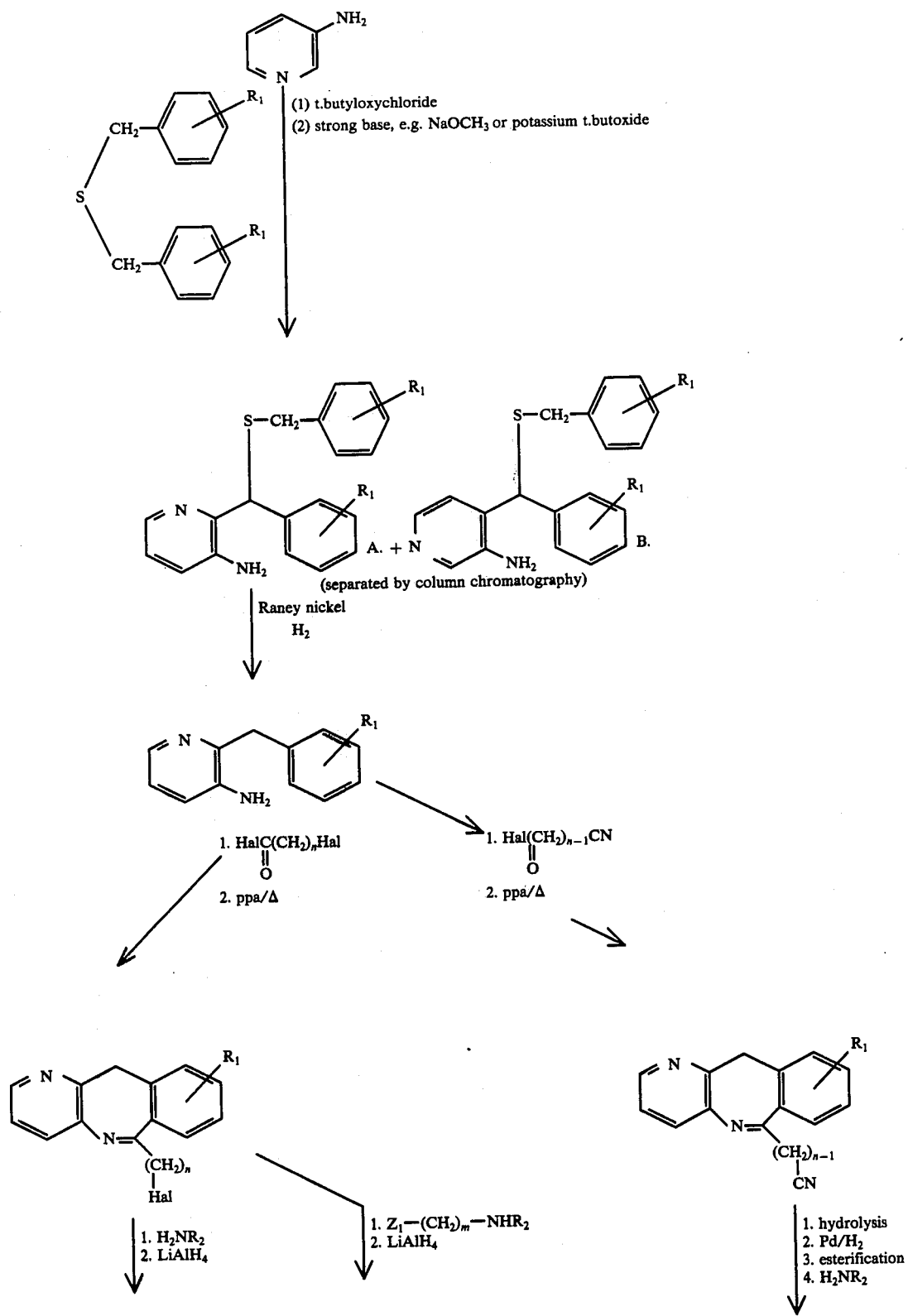

-continued

Flow sheet B; compounds IV, IV A and VI

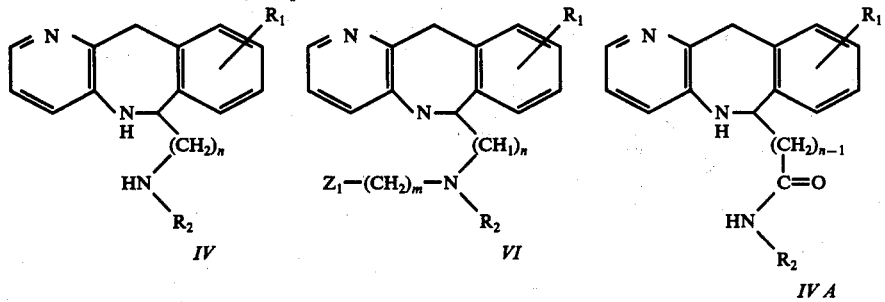

The pharmaceutically acceptable quaternary ammonium compounds, in particular the (1–4 C) alkylammonium salts, are prepared by the reaction of the free base I with e.g. an alkyl halide, such as methyl iodide.

It is naturally possible to introduce or change the substituent $R_1$ in the benzene ring of compound I or to introduce a halogen substituent in the pyridine ring after the above-noted reactions, although the prior presence of these substituents in the above-named starting materials is preferred. It is, for example, possible to prepare compounds I, in which $R_1$ is alkoxy by one of the noted methods, and afterwards convert the alkoxy-group ($R_1$) into a hydroxy group using known methods. A halogenation of a compound I with for instance bromine or chlorine affords mainly a compound I, in which the pyridine ring has been substituted by one halogen atom.

Changing the substituent on the nitrogen atom ($R_2$) of a compound I after the above-noted reactions is however more usual. It is, for example, possible to (ar)alkylate the unsubstituted amine ($R_2 = H$) in the usual way, resulting in a compound with $R_2 = $ (ar)alkyl. This (ar)alkylation can be achieved directly, with, for example, an alkyl halide, or indirectly by acylation with, for example, an acid halide or anhydride, followed by reduction of the carbonyl group in the thus-obtained N-acyl derivative. Preferred methods for the introduction of an N-methyl substituent ($R_2 = CH_3$) are the procedure according to Eschweiler-Clarke or the reaction of a compound I ($R_2 = H$) with formaldehyde and sodium cyanoborohydride in, for example, acetonitrile.

A compound I in which $R_1$ is alkyl or aralkyl can furthermore be converted into a compound I with $R_2$ is H in one of the usual ways described in the literature, for example, by reaction with an alkyl chloroformate such as ethyl chloroformate, or with cyanogen bromide, followed by hydrolysis of the product obtained in this way.

Within the context of this invention, an alkyl group as defined under $R_1$ and $R_2$ is understood to be a branched- or straight-chain alkyl group with 1 - 6 carbon atoms, such as methyl, ethyl, propyl, isopropyl, butyl, isobutyl, tert. butyl, n-pentyl, isopentyl and hexyl.

The alkyl groups of the alkoxy and alkyl-thio groups as defined under $R_1$ and $R_2$ have the same meaning.

By an aralkyl group in the definition of $R_2$ is preferably meant a phenylalkyl group, in which the alkyl group contains 1 - 4 carbon atoms, such as benzyl, phenylethyl, phenylpropyl, phenylisopropyl, phenylbutyl and phenylisobutyl.

For the utilization of the compounds I as biologically active compounds, preference is accorded to the compounds I in which $n = 1$ and $m = 2$ or 3.

EXAMPLE I

The preparation of 2-methyl-1,2,3,4,10,14b-hexahydrobenzo[c]-pyrazino[1,2-a]pyrido[3,2-f]azepine and salts 1. 1-(3-cyanopyridyl-2)-2-phenyl-4-methylpiperazine.

17.43 g (0.3 mol) dry potassium fluoride is added to a solution of 13.85 g (0.1 mol) 2-chloro-nicotinonitrile and 17.62 g (0.1 mol) 1-methyl-3-phenylpiperazine in 250 ml dry DMF and the suspension is heated at 140° C under a nitrogen atmosphere for 20 hours. After cooling, the reaction mixture is poured out into 1,250 ml water.

The aqueous phase is extracted four times with 300 ml ethyl acetate, after which the combined organic extracts are washed with 100 ml water. After drying, the ethyl acetate extracts are evaporated. The crude oil may be used as such for the following step. The nitrile obtained may however also be purified by column chromatography on $SiO_2$, with hexane-acetone (95:5). In this way, 21.9 g (79%) pure 1-(3-cyanopyridyl-2)-4-methyl-2-phenylpiperazine is obtained; the substance crystallizes from petroleum ether 40/60; melting point 66.5°-67.5° C.

$R_f$ in toluene: ethanol (6:4) = 0.74 ($SiO_2$)
$R_f$ in toluene: acetone (6:4) = 0.27 ($SiO_2$).

2. 1-(3-carboxypyridyl-2)-2-phenyl-4-methylpiperazine.

19.5 g (0.07 mol) 1-(3-cyanopyridyl-2)-4-methyl-phenylpiperazine is dissolved in 390 ml of a saturated solution (25 g KOH per 100 ml ethanol). The solution is heated with stirring at 100° C for 24 hours.

After cooling, water (390 ml) is added. The alcohol is evaporated under vacuum and the cloudy solution remaining is extracted twice with 100 ml methylene chloride. The residual aqueous phase is cooled and the pH is adjusted to 7 with dilute (2N) HCl, after which it is extracted with chloroform. After drying the combined chloroform extract, it is reduced to small bulk and 16.2 g 1-(3-carboxy-pyridyl-2)-4-methyl-2-phenylpiperazine is obtained as a colourless oil. Crystallization from ethanol gives a crystalline substance with a melting point of 161°-162° C.

$R_f$ in n.butanol: pyridine: acetic acid: water (4:0.75:0.25:1) = 0.31 on $SiO_2$.

3. 1-(3-hydroxymethylpyridyl-2)-2-phenyl-4-methyl-piperazine.

20.4 g (0.07 mol) 1-(3-carboxypyridyl-2)-2-phenyl-4-methylpiperazine is dissolved in 300 ml dry THF and gradually added with stirring over a period of 1 hour to a boiling suspension of 20.4 g $LiAlH_4$ in 600 ml dry THF under a nitrogen atmosphere. The mixture is boiled under reflux for a further 4 hours, after which it is cooled in an ice-bath and decomposed by carefully adding 81.6 ml water with stirring. The stirring is continued for some time at room temperature, after which the inorganic salts are filtered off. The filtrate is dried and solvent is removed by evaporation, giving a yield of 18.39 g (93%) 1-(3-hydroxymethylpyridyl-2)-2-phenyl-4-methylpiperazine. Recrystallization from ether gives a crystalline product (white needles) of melting point 124°–126° C. $R_f$ in butanol: pyridine: acetic acid: water (4:0.75:0.25:1) = 0.48 on $SiO_2$.

4. 2-methyl-1,2,3,4,10,14b-hexahydro-benzo[c]-pyrazino-[1,2-a]-pyrido[3,2-f]azepine.

6.5 ml concentrated sulphuric acid is added dropwise at room temperature with constant stirring to 3.25 g of the alcohol obtained in 3. During the addition, the temperature rises to about 35° C. The whole is subsequently stirred for a further 2 hours, until a clear homogenous reaction mixture is obtained. This is allowed to stand for a few hours, after which 60 g ice is added and the mixture is made alkaline with concentrated ammonia (22 ml). The reaction mixture is then extracted with chloroform. The chloroform extracts are combined, dried and concentrated. The crude reaction product crystallizes when ether is added, and the solid obtained is recrystallized from petroleum ether 40–60. Yield: 2.43 g; melting point: 114°–116° C.

$R_f$ in methanol: acetic acid (9:1) = 0.48 on $SiO_2$.

Treatment of the thus obtained free base with an alcoholic HCl solution gives the HCl salt of 2-methyl-1,2,3,4,10,14b-hexahydro-benzo[c]pyrazino-[1,2-a]-pyrido[3,2-f]azepine.

Treatment of the free base with methyl iodide provides the corresponding iodomethylate.

EXAMPLE II

The following compounds are prepared in a way corresponding to that described in example I:

a. 1,2,3,4,10,14b-hexahydrobenzo[c]pyrazino[1,2-a]-pyrido[3,2-f]azepine maleate; melting point 187°–190° C, $R_f$ in butanol: acetic acid: water (4:1:1) = 0.47 ($SiO_2$).

b. 12-chloro-2-methyl-1,2,3,4,10,14b-hexahydrobenzo[c]-pyrazino[1,2-a]pyrido[3,2-f]azepine dihydrochloride; melting point 281°–284° C, $R_f$ in toluene: ethanol (8:2) = 0.33 ($SiO_2$).

Melting point maleate: 207°–209° C.

c. 13-chloro-2-methyl-1,2,3,4,10,14b-hexahydrobenzo[c]-pyrazino[1,2-a]pyrido[3,2-f]azepine dihydrochloride; melting point 222°–224° C, $R_f$ in toluene: ethanol (8:2) = 0.44 ($SiO_2$).

Melting point hemisuccinate: 158°–160° C.

d. 12-chloro-2-methyl-1,2,3,4,10,14b-hexahydrobenzo[c]-pyrazino[1,2-a]pyrido[3,2-f]azepine-2-methiodide; melting point 279°–281° C.

e. 12-methoxy-2-methyl-1,2,3,4,10,14b-hexahydrobenzo[c]-pyrazino[1,2-a]pyrido[3,2-f]azepine.

$R_f$ in toluene: ethanol (8:2) = 0.4 ($SiO_2$).

f. 2,11-dimethyl-1,2,3,4,10,14b-hexahydrobenzo[c]-pyrazino-[1,2-a]pyrido[3,2-f]azepine $R_f$ in toluene: ethanol (8:2) = 0.38 on $SiO_2$.

g. 2,13-dimethyl-1,2,3,4,10,14b-hexahydrobenzo[c]-pyrazino[1,2-a]pyrido[3,2-f]azepine.hydrochloride; melting point: 260°–265° C (dec.)

$R_f$ in toluene: ethanol (8:2) = 0.41 ($SiO_2$).

h. 13-hydroxy-2-methyl-1,2,3,4,10,14b-hexahydrobenzo[c]-pyrazino[1,2-a]pyrido[3,2-f]azepine (oil).

EXAMPLE III

Preparation of 2-methyl-1,2,3,4,5,15b-hexahydro-11H-benzo[c][1,4[-diazepine[1,2-a]pyrido[3,2-f]azepine 1. $N^1$-methyl-$N^1$-(3-propionic acid)-2-phenylethylene diamine.

28.8 g $N^1$-methyl-2-phenylethylene diamine is dissolved in 350 ml toluene. 13.3 ml acrylic acid is added to this solution and the mixture is heated with stirring in an oil bath at 60° C for 3 hours. After cooling, the reaction mixture is evaporated under vacuum and the residue is crystallized from ethanol. Yield 33 g; melting point 178°–179° C.

$R_f$ in methanol: acetone (9:1) = 0.75 on $SiO_2$.

2. 2,3,4,5,6,7-hexahydro-1H-1-methyl-3-phenyl-5-oxo-(1,4)-diazepine 33 g of the diamine obtained in 1. is suspended in 900 ml toluene and 70 ml $SOCl_2$ is added with stirring to the suspension, which is then heated to an oil bath at 75° C for 3 hours.

After cooling, the precipitate is filtered off and washed with toluene. This precipitate is then recrystallized from ethanol, after which it is dissolved in the minimum amount of water necessary. The aqueous solution is made alkaline with 33% NaOH, after which it is extracted with ether. The ether layer is evaporated to dryness under vacuum.

Yield 25 g; melting point 123°–125° C.

$R_f$ in methanol: acetone (9:1) = 0.5

3. 2,3,4,5,6,7-hexahydro-1H-1-methyl-3-phenyl-(1,4-diazepine.

16 g lithium aluminium hydride is suspended in 500 ml dry ether. A solution of 16 g of the product from 2. in 200 ml dry tetrahydrofuran (THF) is added dropwise to this suspension. The resultant mixture is then refluxed for 4 hours, after which it is cooled in ice and 64 ml water is slowly added. The white inorganic precipitate is filtered off and washed with THF. The colourless filtrate is evaporated under vacuum. Yield 14.2 g of a colourless oil.

$R_f$ in methanol: acetone (9:1) = 0.1 on $SiO_2$.

4. 1-(3-cyanopyridyl-2)-2-phenyl-4-methyl-2,3,4,5,6,7-hexahydro-1H-(1,4-diazepine.

7 g of the diazepine derivative prepared in 3. in mixed with 7 g 2-fluoro-nicotinonitrile, and 4 g sodium carbonate (anhydrous) is added to this mixture. The whole is then heated in an oil bath at 140° C for 4 hours. After cooling, the mixture is extracted with warm hexane and the extracts are evaporated to dryness. Yield 8.2 g; melting point 83°–86° C.

5. 1(3-carboxypyridyl-2)-2-phenyl-4-methyl-2,3,4,5,6,7-hexahydro-1H-1,4-diazepine.

6 g of the nitrile obtained in 4. is suspended in 100 ml ethanol (96%). 40 g KOH is then added to this suspension and the reaction mixture is then refluxed for 33 hours. After cooling, the reaction mixture is diluted with 300 ml ethanol, and the pH is then adjusted to 6 by addition of a 30% solution of HCl in ethanol. The organic precipitate is filtered off and the filtrate is evaporated under vacuum. The residue is taken up in methylene chloride, after which the methylene chloride is distilled off under vacuum.

Yield 3.6 g; melting point 178°–180° C.

$R_f$ in methanol: acetone (9:1) = 0.4

6. 1-(3-hydroxymethylpyridyl-2)-4-methyl-2-phenyl-2,3,4,5,6,7-hexahydro-1H-1,4-diazepine.

300 mg lithium aluminium hydride is suspended in 40 ml dry ether. A solution of 100 mg of the carboxylic acid from 5. in 40 ml dry ether is then added to this suspension and the whole is refluxed for 2 hours, after which it is cooled in ice and 1.2 ml water is added dropwise. The inorganic precipitate is filtered off and washed with ether. The filtrate is evaporated to dryness under vacuum.

Yield 40 mg of an oil; $R_f$ in methanol:acetone (9:1) = 0.35 on $SiO_2$.

7. 2-methyl-1,2,3,4,5,15b-hexahydro-11H-benzo[c]-[1,4]diazepine[1,2-a]pyrido[3,2-f]azepine monopicrate.

0.5 ml concentrated sulphuric acid is added to 40 mg of the alcohol obtained in 6. and the resultant mixture is heated on a steam bath for 10 minutes. 10 ml iced water (0° C) is then added and the whole is extracted with ether. The acid aqueous layer is made alkaline with 2 N NaOH and extracted with ether. The ether extract is washed with water and solvent is removed under vacuum, giving the title compound as free base (oil).

$R_f$ in butanol: acetic acid: water (4:1:1) = 0.43 on $SiO_2$.

The oily residue is taken up in 0.5 ml ethanol and a solution of picric acid in ethanol is then added to this solution. The precipitate is filtered off and washed with ether.

Yield 20 mg; melting point 205°–208° C.

EXAMPLE IV

Preparation of 2-methyl-1,2,3,4,10,14b-hexahydro-benzo[c]pyrazino[1,2-a]pyrido[3,4-f]azepine.

1.8 g 1-(3-hydroxymethylpyridyl-4)-2-phenyl-4-methylpiperazine, melting point 127°–129° C, prepared in a way analogous to that described in example I, is added in portions to 3.6 ml cooled, concentrated sulphuric acid under nitrogen over a period of about 10 minutes. The mixture is subsequently stirred for about 7 hours at room temperature, until a clear homogeneous reaction mixture has been obtained.

25 g ice is then added to the mixture, after which it is rendered alkaline with concentrated ammonia (about 12 ml). The alkaline mixture is then extracted with ethyl acetate and the ethyl acetate extract thus obtained is dried and evaporated to dryness.

Yield 1.68 g of a colourless oil.

$R_f$ in methanol: acetic acid (9:1) = 0.42 on $SiO_2$.

The compound is treated with picric acid in ethanol, by means of which a crystalline dipicrate is obtained. Melting point 247°–248° C. Treatment with benzoic acid in 95% ethanol gives the benzoic acid salt with 3 molecules of water of crystallization. Melting point 87°–89° C.

EXAMPLE V

The following compounds are prepared in a way corresponding to that described in example IV:
2-methyl-1,2,3,4,5,15b-hexahydro-11H-benzo[c][1,4]-diazepino[1,2-a]pyrido[3,4-f]azepine,
2,13-dimethyl-1,2,3,4,5,15b-hexahydro-11H-benzo[c]-[1,4]diazepino[1,2-a]pyrido[3,4-f]azepine,
2-propyl-1,2,3,4,10,14b-hexahydro-benzo[c]-pyrazino[1,2-a]pyrido[3,4-f]azepine.

EXAMPLE VI

Preparation of 2-methyl-1,2,3,4,10,14b-hexahydro-benzo[c]-pyrazino[1,2-a]pyrido[3,4-f]azepine 1. 2-methyl-10-oxo-1,2,3,4,10,14b-hexahydro-benzo[c]pyrazino[1,2-a]pyrido[3,4-f]azepine.

3.7 g (0.01 mol) 1-(3-carboxypyridyl-4)-4-methyl-2-phenyl-piperazine dihydrochloride (melting point 175°–178° C) is converted into the free base by stirring with 0.57 g KOH in 100 ml ethanol. After stirring at room temperature for 1 hour, the reaction mixture is evaporated to dryness and 30 ml $SOCl_2$ is added to the residual solid. The mixture is refluxed for 4 hours, after which it is evaporated. 50 ml dry 1,2-dichloroethane is added to the residue and the mixture is stirred for a while, after which the insoluble component is filtered off.

The filtrate is subsequently added with stirring, and under nitrogen, to a suspension of 7.5 g anhydrous aluminium chloride in 45 ml carbon disulphide. The reaction mixture is boiled under reflux for 20 hours, after which it is poured into 100 ml water and extracted with methylene chloride. The organic phase is dried and the solvent removed by evaporation, giving 950 mg (34%) crude 2-methyl-10-oxo-1,2,3,4,10,14b-hexahydro-benzo[c]pyrazino[1,2-a]pyrido[3,4-f]azepine as an oily product.

$R_f$ in toluene: ethanol (8:2) = 0.8 on $SiO_2$.

2. 2-methyl-1,2,3,4,10,14b-hexahydro-benzo[c]-pyrazino[1,2-a]pyrido[3,4-f]azepine.

800 mg (0.00285 mol) 2-methyl-10-oxo-1,2,3,4,10,14b-hexahydro-benzo[c]pyrazino[1,2-a]pyrido[3,4-f]azepine is added to a well-stirred suspension consisting of 4 ml di-ethylene glycol, 1 ml DMSO, 0.4 g KOH and 1 ml 80% hydrazine hydrate. The reaction is exothermic; the temperature of the reaction mixture is adjusted to 120° C and held there for 30 minutes. During this period hydrazine/water (0.8 ml) is distilled off, and the reaction temperature is then raised to 160° C for 2 hours. The reaction mixture is subsequently cooled, poured into water, and extracted with ether. After drying, and removing the solvent by evaporation, 685 mg (90%) 2-methyl-1,2,3,4,10,14b-hexahydro-benzo[c]-pyrazino[1,2-a]pyrido[3,4-f]azepine is obtained as a light yellow oil.

Treatment of this oil with benzoic acid in ethanol (95%) gives the crystalline benzoate, melting point 86°–89° C. The substance still contains 3 molecules of water of crystallization.

EXAMPLE VII

The following compounds are prepared in a way corresponding to that described in example VI:
2,12-dimethyl-1,2,3,4,10,14b-hexahydro-benzo[c]-pyrazino[1,2-a]pyrido[3,4-f]azepine,
2-methyl-1,2,3,4,5,15b-hexahydro-11H-benzo[c][1,4]-diazepino[1,2-a]pyrido[3,2-f]azepine,
2-methyl-1,2,3,4,5,15b-hexahydro-11H-benzo[c][1,4]-diazepino[1,2-a]pyrido[3,4-f]azepine,
2-methyl-1,2,3,4,10,14b-hexahydro-benzo[c]-pyrazino[1,2-a]pyrido[3,2-f]azepine,
12-methoxy-2-methyl-1,2,3,4,10,14b-hexahydro-benzo[c]pyrazino[1,2-a]pyrido[3,2-f]azepine.

EXAMPLE VIII 2-methyl-1,2,3,4,10,14b-hexahydro-benzo[c]-
pyrazino[1,2-a]pyrido[2,3-f]azepine.

1. Preparation of benzyl-α-(3-aminopyridyl-2)-benzyl sulphide and benzyl-α-(3-aminopyridyl-4)-benzyl sulphide.

9.41 g 3-aminopyridine (0.1 mol) is dissolved in 400 ml methylene chloride and the solution is cooled to −65° C/-70° C. 10.86 g (0.1 mol) t.butyl hypochlorite in 10 ml methylene chloride is then added during a period of 15 minutes and the mixture is stirred for 25 minutes at this temperature, after which 21.5 g (0.1 mol) dibenzyl sulphide is added. Stirring continues for a further 40 minutes. A freshly prepared solution of 5.02 g sodium in 75 ml methanol is then added to the mixture over a period of 8 minutes. The reaction mixture is subsequently stirred for 1 hour at −65° C/-70° C, after which it is brought up to room temperature. After stirring overnight at 40° C, 5° ml water is added to the mixture, the organic layer ($CH_2Cl_2$) is separated off, and the aqueous phase is extracted twice with methylene chloride. After drying, the combined organic phases are evaporated, giving a dark brown oil consisting predominantly of two components (see compounds A and B in Flow Sheet B. The crude reaction product is purified on an $SiO_2$ column. The first fraction is eluted with toluene/ethyl acetate (95/5); after removal of solvent from the fraction by evaporation, 12.4 g (40%) benzyl-α-(3-amino-pyridyl-2)-benzyl sulphide (A) is obtained as a clear liquid. A second fraction is eluted with toluene/ethyl acetate (1/1); evaporation of this fraction gives 6.3 g (21%) benzyl-α-(3-amino-pyridyl-4)-benzyl sulphide (B) as a solid of melting point 91°-92° C.

$R_f$ in toluene : ethyl acetate (8:2) = 0.53 on $SiO_2$ for compound A and 0.11 for compound B.

2. Preparation of 2-benzyl-3-aminopyridine.

10.2 g (0.033 mol) benzyl-α-(3-aminopyridyl-2)-benzyl sulphide is dissolved in 400 ml ethanol, and 80 g activated Raney nickel is added with stirring to the resultant solution, after which the whole is stirred for 1 hour. The catalyst is then filtered off and rinsed with ethanol. The ethanol phases are then evaporated to dryness, giving 4.78 g (80%) 2-benzyl-3-amino-pyridine as a white solid. The product is recrystallized from ether. Melting point 84°-86° C.

3. Preparation of 2-benzyl-3-chloro-acetamido pyridine.

3.4 ml tri-ethylamine is added to a solution of 4.5 g (0.025 mol) 2-benzyl-3-aminopyridine in 25 ml dry benzene. A solution of 2 ml chloro-acetyl chloride in 40 ml dry benzene is then added with stirring to this solution at a temperature of 5°-10° C. The mixture is stirred for 30 minutes at room temperature and a precipitate forms. This precipitate is redissolved by addition of 50 ml water and 50 ml benzene to the mixture. The organic phase is subsequently separated off, dried, and evaporated to dryness. The residue, a white solid, is recrystallized from a little benzene, giving 5.78 g (92%) 2-benzyl-3-chloro-acetamidopyridine of melting point 145°-147° C.

4. Preparation of 6-chloromethyl-11H-benzo[e]-pyrido[3,2-b]azepine.

5 g (0.0190 mol) 2-benzyl-3-chloro-acetamidopyridine, 12.5 g $P_2O_5$ and 50 ml $POCl_3$ are heated with vigorous stirring in an oil-bath at 120° C for 24 hours. After cooling, ice is cautiously added to the reaction mixture, which is then poured into 500 ml iced water, made alkaline, and extracted with methylene chloride. After drying, solvent is removed from the organic phase by evaporation, giving 4.1 g of a light brown oil, which is chromatographed on an $SiO_2$ column with toluene-/ethyl acetate as eluent. In this way, 2.8 g (60%) 6-chloromethyl-11H-benzo[e]pyrido[3,2-b]azepine is obtained as a clear oil.

$R_f$ is toluene : ethyl acetate (6:4) = 0.31 on $SiO_2$.

5. Preparation of 6-methylaminomethyl-5,6-dihydro-11H-benzo[e]pyrido[3,2-b]azepine.

2.43 g (0.01 mol) 6-chloromethyl]-11H-benzo[e]-pyrido[3,2-b]azepine is dissolved in 25 ml methylamine at −10° C. The reaction mixture is stirred at this temperature for 3 hours, after which excess methylamine is removed by evaporation at room temperature. The intermediate 6-methylaminomethyl-11H-benzo[e]-pyrido[3,2-b]azepine which remains is dissolved in 125 ml dry ether and added with stirring and under nitrogen to a suspension of 1.25 g $LiAlH_4$ in 70 ml dry ether. The reaction mixture is stirred for 2 hours at room temperature. The hydride is subsequently destroyed by the addition of 5 ml water and the inorganic salts are filtered off. The filtrate is then evaporated to dryness and a portion of the residue is recrystallized from $CHCl_3$/hexane. Melting point 120°-122° C. Dissolving the residue in ethanol and adding the resultant solution to a solution of maleic acid (1.2 g) in ethanol gives 2.63 g of the maleate of 6-methylaminomethyl-5,6-dihydro-11H-benzo[e]pyrido[3,2-b]azepine, melting point 138°-140° C.

6. Preparation of 2-methyl-1,2,3,4,10,14b-hexahydro-benzo[c]pyrazino[1,2-a]pyrido[2,3-f]azepine.

2.4 g (0.01 mol) 6-methylaminomethyl-5,6-dihydro-11H-benzo[e]pyrido[3,2-b]azepine in 7 ml tri-ethylamine is added under nitrogen to 100 ml 1,2-dibromoethane, preheated to 100° C. The reaction mixture is stirred for 30 minutes at 100°-105° C, after which it is cooled to 20° C. Insoluble salts are filtered off, and the filtrate is washed with water, dried, and evaporated to dryness. Yield 2.5 g (oil).

$R_f$ in butanol : acetic acid : water (4:1:1) = 0.20 $SiO_2$.
Melting point maleate: 162°-165° C (dec.).

EXAMPLE IX 2-methyl-1,2,3,4,10,14b-hexahydro-benzo[c]-
pyrazino[1,2-a]pyrido[4,3-f]azepine 1. Preparation of 10-methylaminomethyl-10,11-dihydro-5H-benzo[e]pyrido[3,4-b]azepine.

The product benzyl-α-(3-aminopyridyl-4)-benzyl sulphide (B) obtained in example VIII.1. is converted into 10-methylaminomethyl-10,11-dihydro-5H-benzo[e]-pyrido[3,4-b]azepine in a way corresponding to that described in Example VIII, (2–5 inclusive).

2. Preparation of 2-methyl-1,2,3,4,10,14b-hexahydro-benzo[c]pyrazino[1,2-a]pyrido[4,3-f]azepine.

The diamine obtained in 1 is converted into the abovenoted final product with dibromo-ethane and tri-ethylamine in a way corresponding to that described in Example VIII 6.

EXAMPLE X 2-methyl-1,2,3,4,10,14b-hexahydro-benzo[c]-
pyrazino[1,2-a]pyrido[2,3-f]azepine.

1. Preparation of 2-methyl-3,4-dioxo-1,2,3,4,10,14b-hexahydro-benzo[c]pyrazino[1,2-a]pyrido[2,3-f]azepine.

2.39 g (0.01 mol) 6-methylaminomethyl-5,6-dihydro-11H-benzo[e]pyrido[2,3-b]azepine is suspended in 2 ml di-ethyl oxalate. The reaction mixture is subsequently warmed to 120° C and the ethanol produced during the reaction is distilled off. The temperature is then raised to 140° C in 15 minutes. The crystalline mass obtained is cooled to 50° C, 10 ml toluene is added, and the reaction mixture is stirred for a further hour at room temperature. The crystalline 2-methyl-3,4-dioxo-1,2,3,4,10,14b-hexahydro-benzo[c]pyrazino[1,2-a]pyrido[2,3-f]azepine is filtered off.

Yield 1.92 g (66%). Melting point 211°–217° C.

$R_f$ in methylenechloride : methanol (9:1) = 0.58 on $SiO_2$.

2. 2-methyl-1,2,3,4,10,14b-hexahydro-benzo[c]pyrazino[1,2-a]pyrido[2,3-f]azepine.

1.46 g (0.005 mol) 2-methyl-3,4-dioxo-1,2,3,4,10,14b-hexahydro-benzo[c]pyrazino[1,2-a]pyrido[2,3-f]azepine is added cautiously to a suspension of 0.4 g $LiAlH_4$ in 25 ml dry dioxan under nitrogen at 25° C. The reaction mixture is boiled under reflux for 2 hours, after which it is cooled to 15° C. 5 ml water is then added, and the inorganic salts are filtered off and rinsed with dioxan. The filtrate is evaporated to dryness, giving a yellow oil. Melting point maleate salt: 163°–164° C (dec.).

EXAMPLE XI

The following compounds are prepared in a way analogous to that described in example X:
2-propyl-1,2,3,4,10,14b-hexahydro-benzo[c]pyrazino[1,2-a]pyrido[2,3-f]azepine,
2,12-dimethyl-1,2,3,4,10,14b-hexahydro-benzo[c]pyrazino[1,2-a]pyrido[2,3-f]azepine,
2-benzyl-1,2,3,4,10,14b-hexahydro-benzo[c]pyrazino[1,2-a]pyrido[2,3-f]azepine,
2-methyl-12-chloro-1,2,3,4,10,14b-hexahydro-benzo[c]pyrazino[1,2-a]pyrido[4,3-f]azepine,
3-methyl-1,2,3,4,5,15b-hexahydro-11H-benzo[c][1,4]-diazepino[1,7-a]pyrido[2,3-f]azepine.

EXAMPLE XII 2-methyl-1,2,3,13b-tetrahydro-9H-benzo[c]imidazo[1,5-a]pyrido[2,3-f]azepine.

4.78 g (0.02 mol) 6-methylaminomethyl-5,6-dihydro-11H-benzo[e]pyrido[2,3-b]azepine is dissolved in 200 ml ethanol in an ampoule and 75 ml formalin (37% aqueous solution) is added. The ampoule is heat-sealed and heated for 3 hours at 100° C, after which it is cooled, opened with care, and the contents are poured out into 500 ml water. After removal of the ethanol by evaporation, the aqueous phase is extracted three times with ether and the ether extracts are dried and evaporated to dryness. The residue weighs 4.53 g and is purified by chromatography on an $SiO_2$ column with toluene/ethanol (8:2) as eluent. This gives 2.23 g (45%) 2-methyl-1,2,3,13b-tetrahydro-9H-benzo[c]imidazo[1,5-a]pyrido[2,3-f]azepine as a clear, pale yellow oil, which crystallises after some time.

Melting point 127°–129° C.

$R_f$ in toluene : ethanol (1:1) = 0.63 on $SiO_2$.

EXAMPLE XIII

The following compounds are prepared in a way corresponding to that of Example XII:
2-methyl-1,2,3,13b-tetrahydro-9H-benzo[c]imidazo[1,5-a]pyrido[4,3-f]azepine;
3-methyl-1,2,3,4,10,14b-hexahydro-benzo[c]pyrimidino[1,6-]pyrido[4,3f]azepine,
3-methyl-1,2,3,4,10,14b-hexahydro-benzo[c]pyrimidino[1,6-a]pyrido[2,3-f]azepine,
4-methyl-1,2,3,4,5,15b-hexahydro-11H-benzo[c][1,3]-diazepino[1,7-a]pyrido[2,3-f]azepine.

EXAMPLE XIV 1,2,3,13b-tetrahydro-9H-benzo[c]imidazo[1,5-a]pyrido[2,3-f]azepine 4.51 g (0.02 mol) 6-aminomethyl-5,6-dihydro-11H-benzo-[e]pyrido[2,3-b]azepine is taken up in 35 ml carbon disulphide. The mixture is refluxed for 45 hours, after which the solvent is distilled off and the yellow residue, 3.65 g 3-thioxo-1,2,3,13b-tetrahydro-9H-benzo[c]imidazo[1,5-a]pyrido[2,3-f]azepine, is stirred in a boiling suspension of 10 g $LiAlH_4$ in 300 ml dry ether for 3 hours. The reaction mixture is worked up in the way described in example X 2., giving 2.8 g of a pale yellow oil.

$R_f$ in toluene : ethanol (1:1) = 0.45 on $SiO_2$.

EXAMPLE XV 2-methyl-1,2,3,13b-tetrahydro-9H-benzo[c]imidazo[1,5-a]pyrido[2,3-f]azepine.

24.3 g 6-methylaminomethyl-5,6-dihydro-11H-benzo[c]pyrido[2,3-b]azepine and 18 g tri-ethylamine are dissolved in 200 ml chloroform, and a solution of 20 g phosgene in 200 ml chloroform is added dropwise with stirring.

Half the chloroform is then removed under vacuum and the liquid remaining is refluxed for 1 hour. The crystal-paste is transferred to a separating funnel and washed consecutively with water, 2 N ammonia and finally water again. The solution, freed in this way from salts and phosgene, is evaporate to dryness under vacuum. The crude 3-oxo compound obtained is dissolved in 400 ml tetrahydrofuran and added to a suspension of 30 g $LiAlH_4$ in 100 ml tetrahydrofuran. The mixture is boiled with stirring for 15 hours, cooled in an ice bath, and the residual hydride is finally destroyed with 120 ml water. The inorganic material is then filtered off and the filtrate is evaporated to dryness, giving 15.3 g 2-methyl-1,2,3,13b-tetrahydro-9H-benzo[c]imidazo[1,5-a]pyrido[2,3-f]azepine as an oil.

$R_f$ in toluene : ethanol (1:1) = 0.60 on $SiO_2$.

EXAMPLE XVI 2-methyl-1,2,3,4,5,15b-hexahydro-11H-benzo[c][1,4]-diazepino[1,2-a]pyrido[2,3-f]azepine.

1. Preparation of 2-methyl-5-oxo-1,2,3,4,5,15b-hexahydro-11H-benzo[c][1,4]diazepino[1,2-a]pyrido[2,3-f]azepine.

3.29 g (0.01 mol) 6-methylaminomethyl-5,6-dihydro-11H-benzo[e]pyrido[2,3-b]azepine is stirred with 0.8 ml (0.011 mol) acrylic acid at 90° C for 1 hour. At the same temperature, 10 ml phosphorus oxychloride is added and the mixture is held at 90° C for a further 2 hours. The reaction mixture is then poured onto 60 g ice with stirring, after which it is stirred for two hours at room temperature. The precipitate formed is filtered off and washed with water until the washings are neutral, after which it is boiled with 20 ml acetone, filtered off, and dried. This gives 1.80 g (49%) 2-methyl-5-oxo-1,2,3,4,5,15b-hexahydro-11H-benzo[c][1,4]- diazepino[1,2-a]pyrido[2,3-f]azepine dihydrochloride, which melts at 264°–270° C with sublimation.

2. Preparation of 2-methyl-1,2,3,4,5,15b-hexahydro-11H-benzo[c][1,4]diazepino[1,2-a]pyrido[2,3-f]azepine.

1.46 g (0.05mol) 2-methyl-5-oxo-1,2,3,4,5,15b-hexahydro-11H-benzo[c][1,4]diazepino[1,2-a]pyrido[2,3-f]azepine is added to a suspension of 1.5 g LiAlH$_4$ in 15 ml dry dioxan under nitrogen, and the whole is stirred for 10 minutes at room temperature, after which the reaction mixture is worked up in the way described in example X.2., giving 1.21 g (89%) 2-methyl-1,2,3,4,5,15b-hexahydro-11H-benzo[c][1,4]-diazepino[1,2-a]pyrido[2,3-f]azepine as a clear colourless oil.

In the same manner are prepared:
2,14-dimethyl-1,2,3,4,5,15b-hexahydro-11H-benzo[c][1,4]diazepino[1,2-a]pyrido[2,3-f]azepine;
2-methyl, 14-trifluoromethyl-1,2,3,4,5,15b-hexahydro-11H-benzo[c][1,4]diazepino[1,2-a]pyrido[2,3-f]azepine.

EXAMPLE XVII 1,2,3,4,10,14b-hexahydro-benzo[c]pyrazino[1,2-a]pyrido-[3,2-f]azepine.

1. A solution of 5.3 g 2-methyl-1,2,3,4,10,14b-hexahydro-benzo[c]pyrazino[1,2-a]pyrido[3,2-f]azepine in 35 ml benzene is added to 6 ml ethyl chloroacetate in 40 ml benzene. The mixture is boiled under reflux for 20 hours, after which it is filtered and the filtrate is extracted with 2 N hydrochloric acid. The acid extract thus obtained is then made alkaline with 2 N NaOH, and the alkaline solution is extracted with ethyl acetate. The ethyl acetate extracts are dried and evaporated to dryness, giving 5 g of the 2-carboxyethyl compound,( oil ).

$R_f$ in toluene : ethanol (8:2) = 0.43 on SiO$_2$.

2. The compound obtained in 1. is stirred for 20 hours with 50 ml concentrated HCl in an oil bath at 110° C. The solution is then cooled and made alkaline with 4 N NaOH, after which it is extracted with ether and the ether extracts are washed with water, dried and the solvent removed by evaporation. The residual oil is chromatographed with methanol/acetone (9:1) on a silica gel column. The purified oil is then treated with a solution of 1.78 g maleic acid in 100 ml acetone, resulting in crystallization of the maleate-salt of the title compound. After recrystallization from ethanol, 3.6 g of the maleate salt is obtained.

Melting point 188°–190° C.

$R_f$ in butanol : acetic acid : water (4:1:1) = 0.47 on SiO$_2$.

EXAMPLE XVIII 8-bromo-2-methyl-1,2,3,4,10,14b-hexahydro-benzo[c]pyrazino[1,2-a]pyrido[3,2-f]azepine To a solution of 5 g (0.0199 mol) 2-methyl-1,2,3,4,10,14b-hexahydro-benzo[c]pyrazino[1,2-a]pyrido[3,2-f]azepine in 100 ml glacial acetic acid are added 5 ml Br$_2$ in 10 ml acetic acid, maintaining the temperature below 15° C. The reaction mixture is stirred at this temperature for 3 hours. The precipitated HBr-salt is collected and washed with acetic acid. The salt is suspended in water and liberated by addition of 2 N NaOH. The aqueous phase is extracted with ethylacetate; the combined organic layers are dried and evaporated, giving a reddish oil (6.84 g). The oil is crystallised from methanol and recrystallised from n.hexane, giving 3.3 g (50%) 8-bromo-2-methyl-1,2,3,4,10,14b-hexahydro-benzo[c]pyrazino[1,2-a]pyrido[3,2-f]azepine as a white crystalline solid. Melting point 126°–128° C.

$R_f$ in methanol: acetone (9:1) = 0.6 (SiO$_2$).

EXAMPLE XIX

Optical resolution of 2-methyl-1,2,3,4,10,14b-hexahydro-benzo[c]-pyrazino[1,2-a]pyrido[3,2-f]azepine.

10 g dl-2-methyl-1,2,3,4,10,14b-hexahydro-benzo[c]-pyrazino[1,2-a]pyrido[3,2-f]azepine are dissolved in 150 ml ethanol (36%). A solution of 14.2 g (0.0378 mol) (−) O,O-dibenzoyltartaric acid in 100 ml ethanol is added under stirring, as well as 250 ml ether. The solution is stirred at 20° C for 60 hours. The white crystalline salt formed is filtered off. Melting point 151°–153° C; $[\alpha]_D^{20}$ = −257°($c$ = 0.1 in methanol). The free base of the crude laevorotatory antipode is obtained upon liberation of the salt with ammonia, extraction with ether, evaporation of the organic phase and crystallisation from petroleum ether 40/60. The same procedure as described before is repeated on the crude free base, giving finally 2.5 g (50%) of (−) 2-methyl-1,2,3,4,10,14b-hexahydrobenzo[c]-pyrazino[1,2-a]pyrido[3.2-f]azepine, melting point 86°–88° C; $[\alpha]_D^{20}$ = −512° (CH$_3$OH; $c$ = 0.1).

The corresponding dextrarotatory antipode is obtained in the same manner, using (+)O,O-dibenzoyltartaric acid as the resolving agent.

(+) 2-methyl-1,2,3,4,10,14b-hexahydro-benzo[c]-pyrazino[1,2-a]pyrido[3,2-f]azepine. Melting point 86°–88° C $[\alpha]_D^{20}$ = +512° ($c$ = 0.1; methanol).

I claim:

1. A compound of the formula:

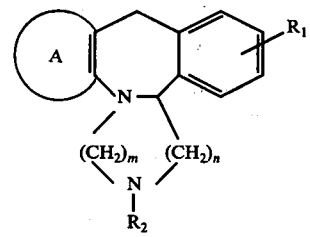

an acid addition salt thereof of a pharmaceutically acceptable acid, or a pharmaceutically acceptable quaternary ammonium salt thereof, in which A represents pyridine or halogen-substituted pyridine, R$_1$ respresent hydrogen, alkyl having 1 to 6 carbon atoms, alkoxy having 1 to 6 carbon atoms, alkylthio having 1 to 6 carbon atoms, halogen, OH, SH or CF$_3$, R$_2$ represents hydrogen, alkyl having 1 to 6 carbon atoms or phenylalkyl, the alkyl of which has 1 to 4 carbon atoms, and $n$ and $m$ represent the values 1, 2 or 3, with the proviso that the sum of $n + m$ must be 2, 3 or 4.

2. A compound according to claim 1, in which $n$ has the value 1 and $m$ is 2 or 3.

3. A compound of the formula:

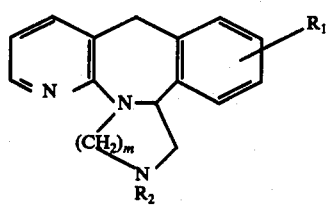
or a salt thereof, in which
R₁, R₂ and m have the meanings indicated in claim 1.
4. The compound:
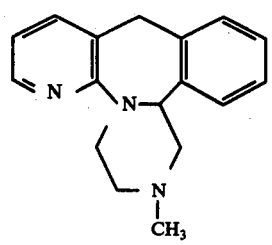
* * * * *

UNITED STATES PATENT AND TRADEMARK OFFICE

CERTIFICATE EXTENDING PATENT TERM
UNDER 35 U.S.C. § 156

PATENT NO.      :   4,062,848

ISSUED          :   December 13, 1977

INVENTOR(S)     :   Willem Jacob van der Burg

PATENT OWNER    :   Akzona Incorporated

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Two years from June 14, 1996, the date the product mirtazapine received approval for commercial marketing or use, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
   Commissioner of Patents and Trademarks